(12) United States Patent
Eick et al.

(10) Patent No.: US 6,955,674 B2
(45) Date of Patent: Oct. 18, 2005

(54) MEDICAL ABLATION CATHETER CONTROL

(75) Inventors: Olaf J. Eick, Willich (DE); John C. M. J. Feron, Sittard (NL)

(73) Assignee: Medtronic, Inc., Minneapolis, MN (US)

( * ) Notice: Subject to any disclaimer, the term of this patent is extended or adjusted under 35 U.S.C. 154(b) by 85 days.

(21) Appl. No.: 10/407,905

(22) Filed: Apr. 7, 2003

(65) Prior Publication Data

US 2004/0127894 A1 Jul. 1, 2004

Related U.S. Application Data

(60) Provisional application No. 60/371,543, filed on Apr. 11, 2002.

(51) Int. Cl.[7] .............................................. A61B 18/04
(52) U.S. Cl. ............................ 606/34; 606/32; 606/41; 606/42; 606/38
(58) Field of Search ..................................... 606/32–50

(56) References Cited

U.S. PATENT DOCUMENTS 5,983,126 A * 11/1999 Wittkampf ................... 600/509
6,427,314 B1 * 8/2002 Acker .......................... 29/503
6,666,863 B2 * 12/2003 Wentzel et al. ............... 606/41

* cited by examiner

Primary Examiner—Roy D. Gibson
Assistant Examiner—Matthew J Kasztejna
(74) Attorney, Agent, or Firm—Girma Wolde-Michael; Paul H. McDowall

(57) ABSTRACT

The control for an ablation catheter provides increased ablation catheter operation feedback and increased options for programmable control of the ablation catheter for clinicians. The control for an ablation catheter has a microcontroller containing memory, an input and output coupled to the microcontroller, a movement program, a comparison program, and an annunciating program. The movement program processes position information from the input to calculate ablation catheter movement. The comparison program compares ablation catheter movement to a predetermined control data.

19 Claims, 16 Drawing Sheets

MEDICAL ABLATION CATHETER CONTROL

RELATED APPLICATION

This application claims priority to provisional U.S. application Ser. No. 60/371,543 filed Apr. 11, 2002.

FIELD OF THE INVENTION

This disclosure is in the field of medical devices and specifically ablation catheters that typically use radio frequency energy to lesion tissue.

BACKGROUND OF THE INVENTION

Radio frequency (RF) ablation catheters have proven to be a very effective treatment for several cardiac tachyarrhythmias. An example of an RF ablation catheter is described in the brochure entitled Medtronic ATAKR® II Advanced RF Ablation System (2000) available from Medtronic, Inc. Minneapolis, Minn. During an ablation procedure an ablation catheter is introduced into the heart usually via the femoral vein or artery under local anesthesia. A position locating system such as described in the brochure entitled Medtronic Model 9670000 LocaLisa® Intracardiac Navigation System. Certain electrogram characteristics, recorded also via an ablation electrode and additional ring electrodes, allow the physician to locate the area of tachycardia origin and the subsequent energy delivery results in thermal destruction of the arrhythmogenic substrate. The size of the demarcated lesion can be controlled by selecting a certain target temperature and appropriate power limits. The damage of arrhythmogenic substrate is a curative treatment and results in immediate and permanent termination of the arrhythmia making any concomitant palliative treatment such as medication unnecessary.

The clinician typically directly controls power to the ablation catheter by control settings on the RF generator and by an on-off switch operated by the clinician's foot. Clinician direct control of the power delivered to the ablation catheter can be inadequate if the catheter dislocates from the intended ablation position. In some circumstances, ablation catheter dislocation can occur so rapidly that the clinician does not have time to properly respond. Additionally, ablation systems such as the Medtronic ATAKR® II do not provide feedback to the clinician other than ablation catheter tip temperature. Catheter dislocation during RF delivery may result in an unintentional heating of healthy non-arrhythmogenic tissue. For example, catheter ablation to treat Atrial Ventricular Nodal Reentrant Tachycardia (AVNRT) involves an ablation target close to the physiological atrio-ventricular (AV) node, and damage of healthy non-arrhythmogenic tissue in this area can result in complete AV-block and pacemaker dependency. During temperature-controlled ablation, power is continuously adjusted to maintain a preset target temperature. During catheter dislocation electrode temperature will suddenly decrease and as a consequence power will be automatically increased. Increased power to the ablation catheter results in increased electrode temperature that can create a risk to healthy tissue that might come in contact with the electrode.

For the foregoing reasons, there is a need for a medical ablation catheter control that provides increased ablation catheter operation feedback to the clinician and provides the clinician with increased options for programmable control of the ablation catheter.

SUMMARY OF THE INVENTION

A medical ablation catheter control provides increased ablation catheter operation feedback to a clinician and increased options for programmable control of the ablation catheter. The control for an ablation catheter has a microcontroller containing memory, an input and output coupled to the microcontroller, a movement program processing position information from the input to calculate ablation catheter movement, a comparison program to compare ablation catheter movement to predetermined control data, and an annunciating program to indicate the relation of ablation catheter movement to the predetermined control data through the output. The movement program processes position information from the input to calculate ablation catheter movement. The comparison program compares ablation catheter movement to a predetermined control data. Some embodiments of the medical ablation catheter control can include a control program to determine when ablation catheter movement exceeds a predetermined movement range. Some embodiments can include a response program to interrupt power to the ablation catheter when ablation catheter movement exceeds the predetermined movement range. Many other embodiments of the medical ablation control catheter are possible.

DETAILED DESCRIPTION OF THE INVENTION

Figure 1:
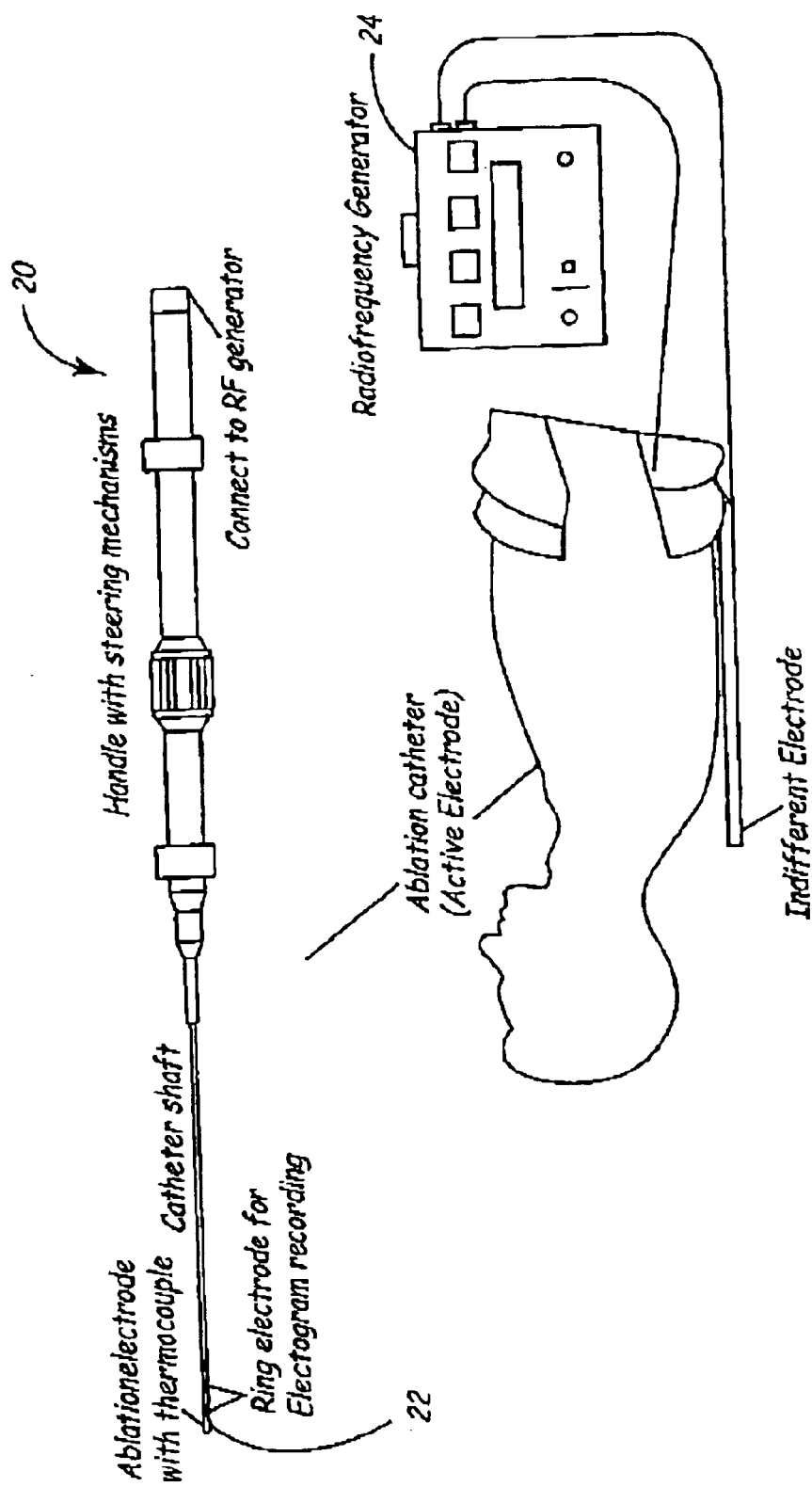
FIG. 1 shows an environment of a medical ablation catheter.

FIG. 1 shows the environment of a medical ablation catheter 20. The medical ablation catheter 20 can be any of a variety of commercial available ablation catheters such as a Medtronic Model RF Conductr® MC available from Medtronic, Inc. Minneapolis, Minn. USA, and the like. The handle of the ablation catheter provides steering capabilities of the catheter distal tip 22. The ablation catheter 20 is connected to a radio frequency (RF) source 24 such as a Medtronic Atakr® II RF generator and the like. The RF generator delivers RF energy typically at a frequency of 480 kHz to the distal tip 22 of the ablation catheter 20. An indifferent electrode that is in contact with the patient's body and connected to the RF source provides the current return path.

Figure 2:
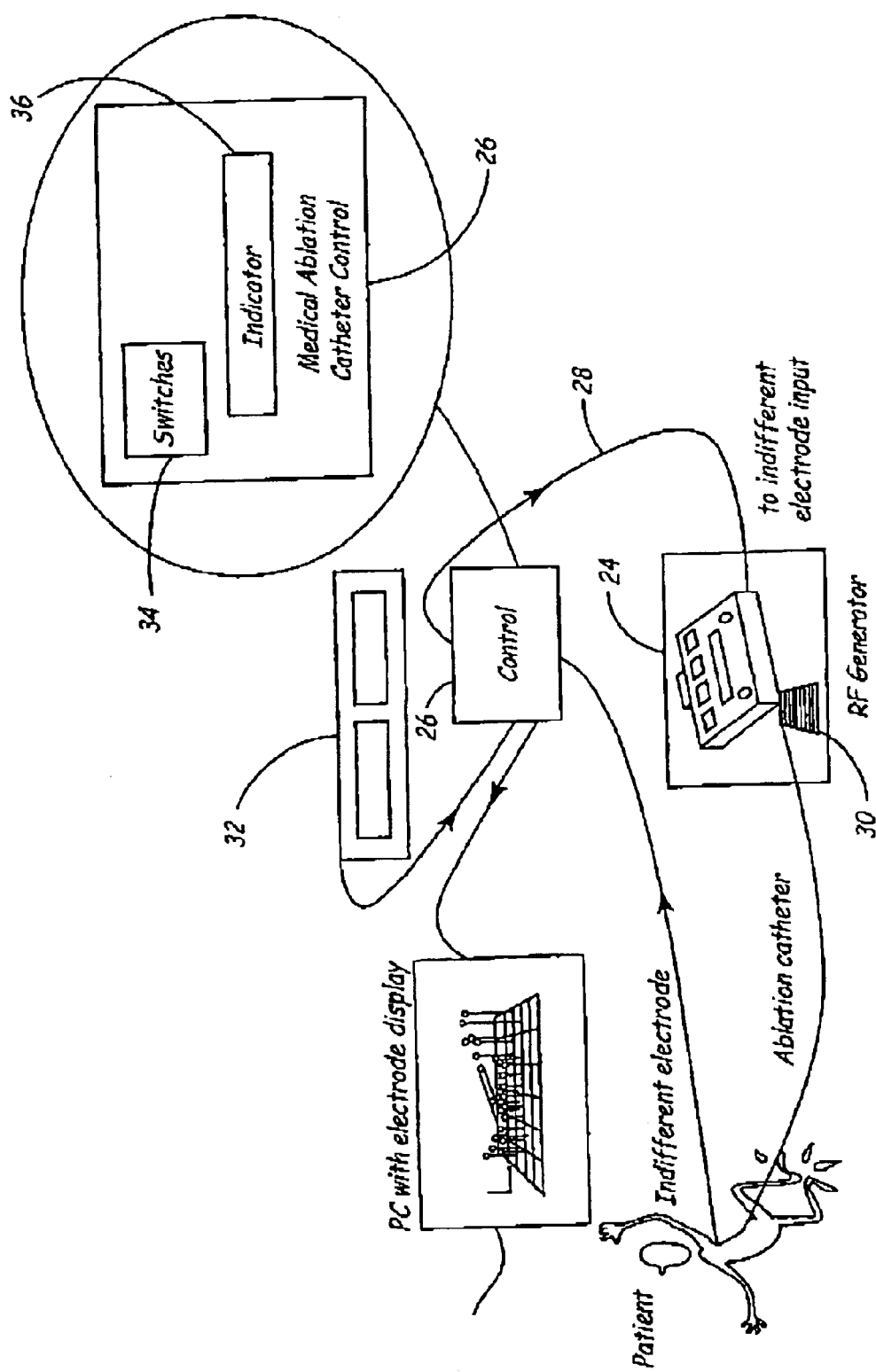
FIG. 2 shows a block diagram of a medical ablation catheter control.

FIG. 2 shows a schematic drawing of a medical ablation catheter control 26 in use. The medical ablation catheter control 26 is connected between the RF source 24 indifferent electrode input 28 and the patient indifferent electrode 30 that is in contact with the patient. Furthermore, the medical ablation catheter control 26 is connected to an electronic position detection system 32, such as a Medtronic Model 9670000 LocaLisa® and a computer for graphical display of the electrode position. The medical ablation catheter control 26 comprises switches 34 to select operational parameters such as allowed movement boundaries and the like and indicators 36 that annunciate the status of the program residing in memory that calculates catheter 20 movement.

Figure 3:
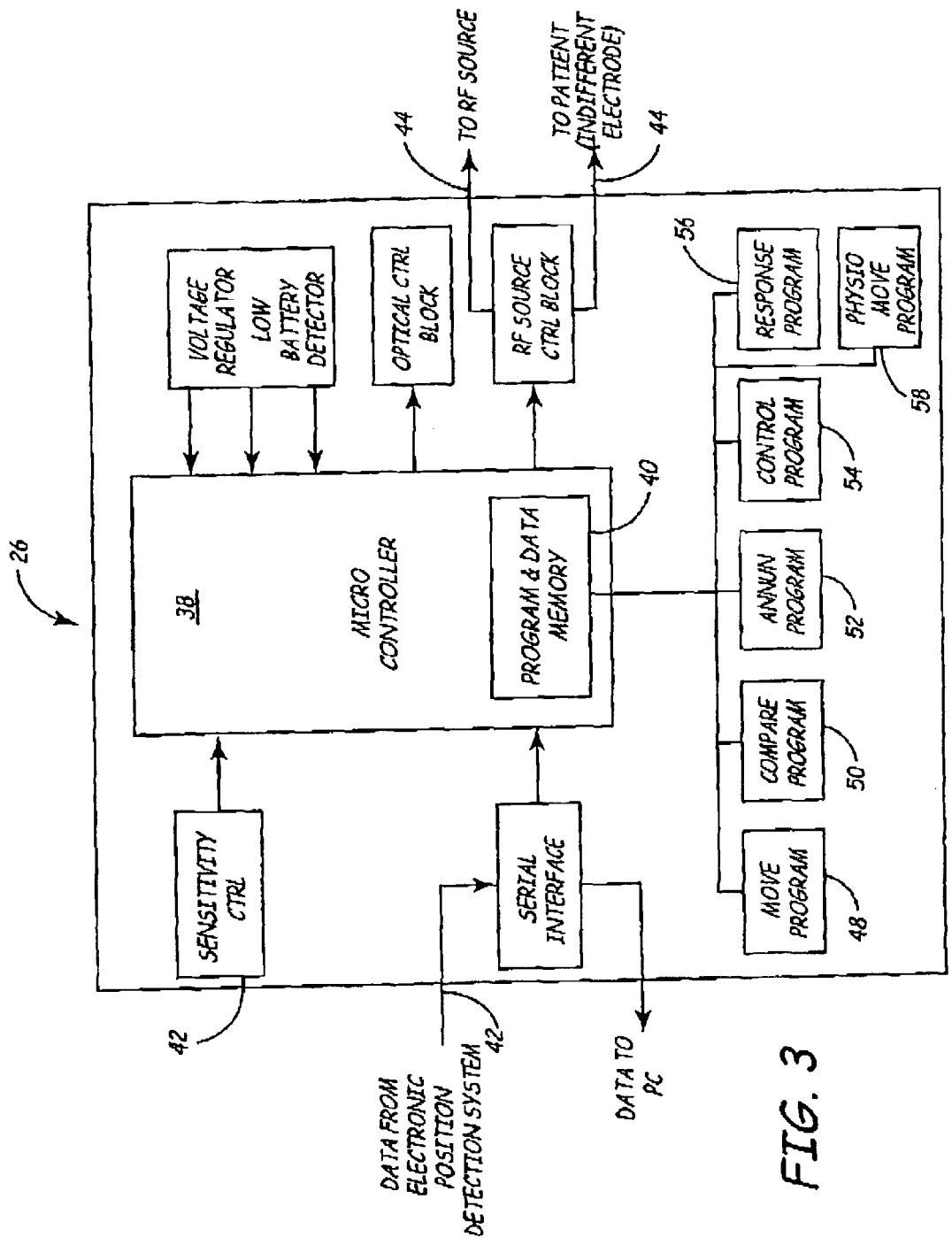
FIG. 3 shows a block diagram of the medical ablation catheter control box.
Figure 4:
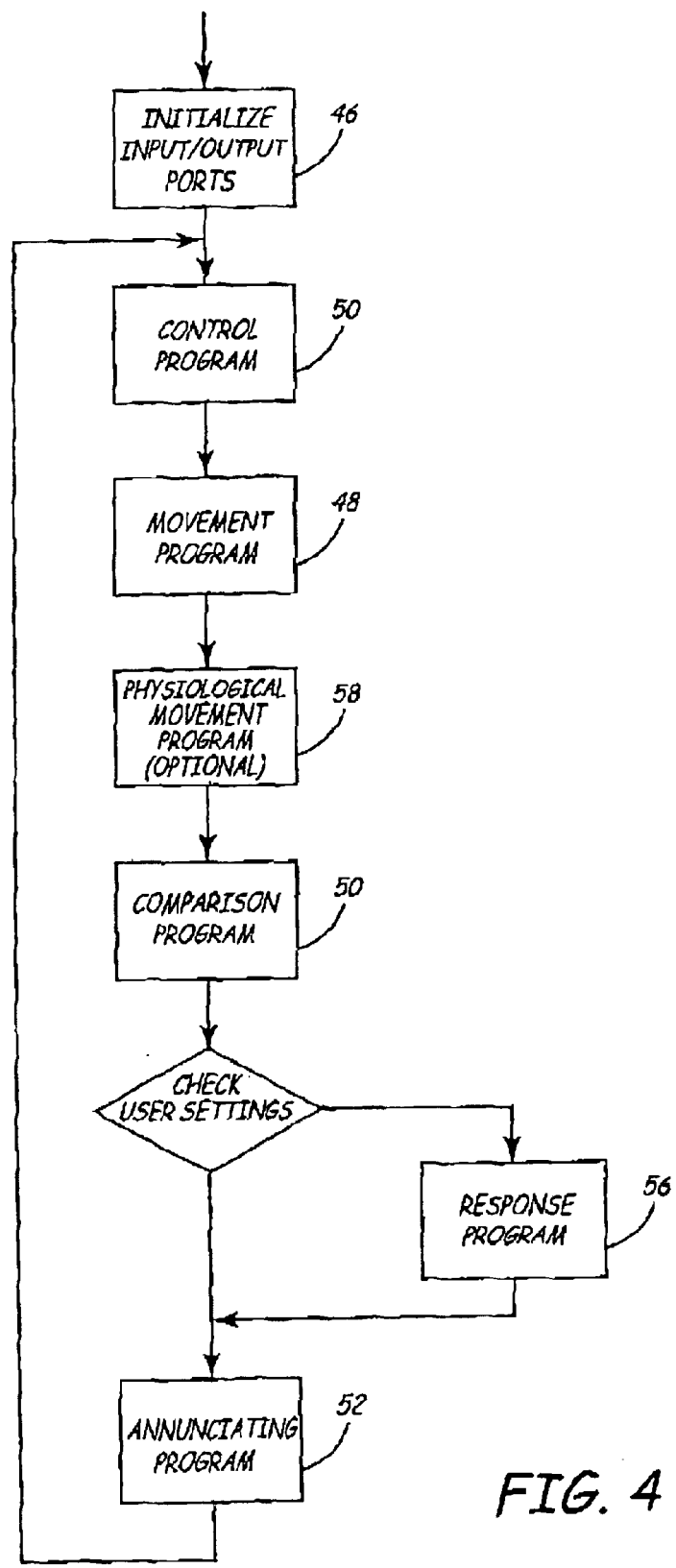
FIG. 4 shows an operational flowchart of the medical ablation catheter control.

FIG. 3 shows a block diagram of the medical ablation catheter control 26, and FIG. 4 shows an operational flowchart of the medical ablation catheter control 26. The medical ablation catheter control 26 comprises a microcontroller 38 containing program and data memory 40 and digital inputs and outputs. The microcontroller 38 can be a Microchip PIC 16F877 and the like. The inputs 42 are coupled to the microcontroller 38 and configured for receiving position information of an ablation catheter 20 from an electronic position detection system 32. More specifically, the inputs 42 can include a low battery detection signal, sensitivity control setting being such as allowed electrode movement boundaries and the like, and a serial data input reading X, Y, and Z electrode from the electronic position detection system. LocaLisa uses real-time 3-dimensional (3D) localization of intracardiac catheter electrodes as described in U.S. Pat. No. 5,983,126 "Catheter location system and method" by Wittkampf (9 Nov. 1999). This method uses an externally applied electrical field that is detected via standard catheter electrodes. Three skin-electrode pairs are used to send three small, 1.0 mA currents through the thorax in three orthogonal directions, with slightly different frequencies of 30 kHz used for each direction. The resulting voltage can be recorded via standard catheter electrodes and be used to determine electrode position.

The output 44 is coupled to the microcontroller 38 and configured for communicating ablation catheter 20 movement. The output 44 can include multiple outputs 44 such as an optical control block controlling the annunciating data signals, an RF source control block that terminates RF energy and the serial data output containing X, Y, Z electrode position information to the computer for graphical display of the electrode position. The medical ablation catheter control 26 includes software residing in program memory inside the microcontroller 38. The software comprises an initialization program 46 for initializing microcontroller hardware, a movement program 48, a comparison program 50, and an annunciating program 52. Some embodiments of the medical ablation catheter control 26 can include a control program 54, a response program 56, and a physiological movement program 58.

Figure 5:
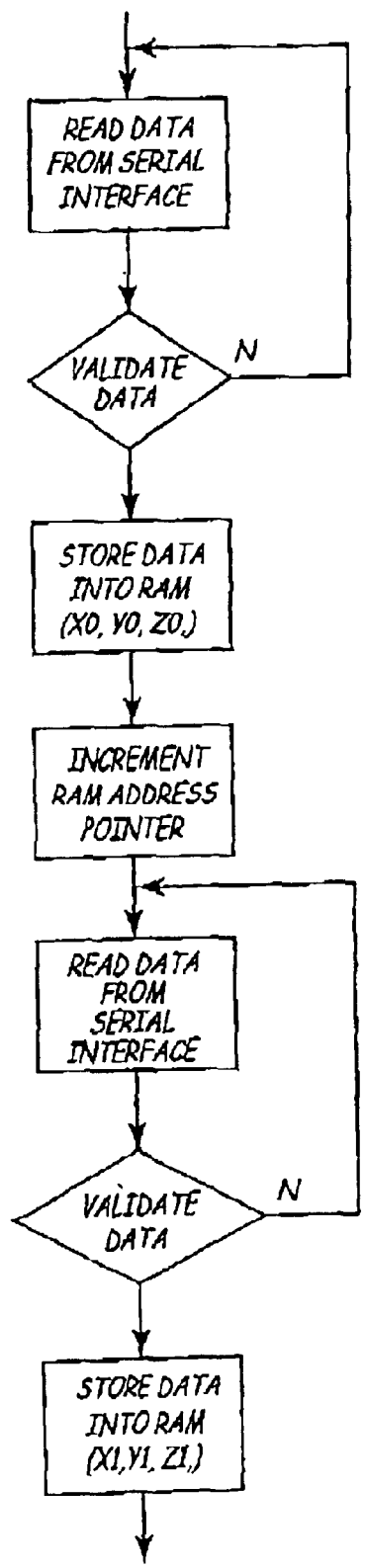
FIG. 5 shows a flowchart of a movement program.

FIG. 5 shows a flowchart of the movement program 48. The movement program 48 resides in memory 40 and reads position information from the input 42 (also know as a serial interface) to calculate ablation catheter movement. In some embodiments, the movement program 48 can read two frames of electrode position information from the input 42, validate this data, and store data into internal data memory 40. The second frame of data is stored in a different location of memory 40 by incrementing a Random Access Memory (RAM) address pointer. At least two frames of electrode position information are stored, so the comparison program 50 can calculate a change in location (FIGS. 6–7).

Figure 6:
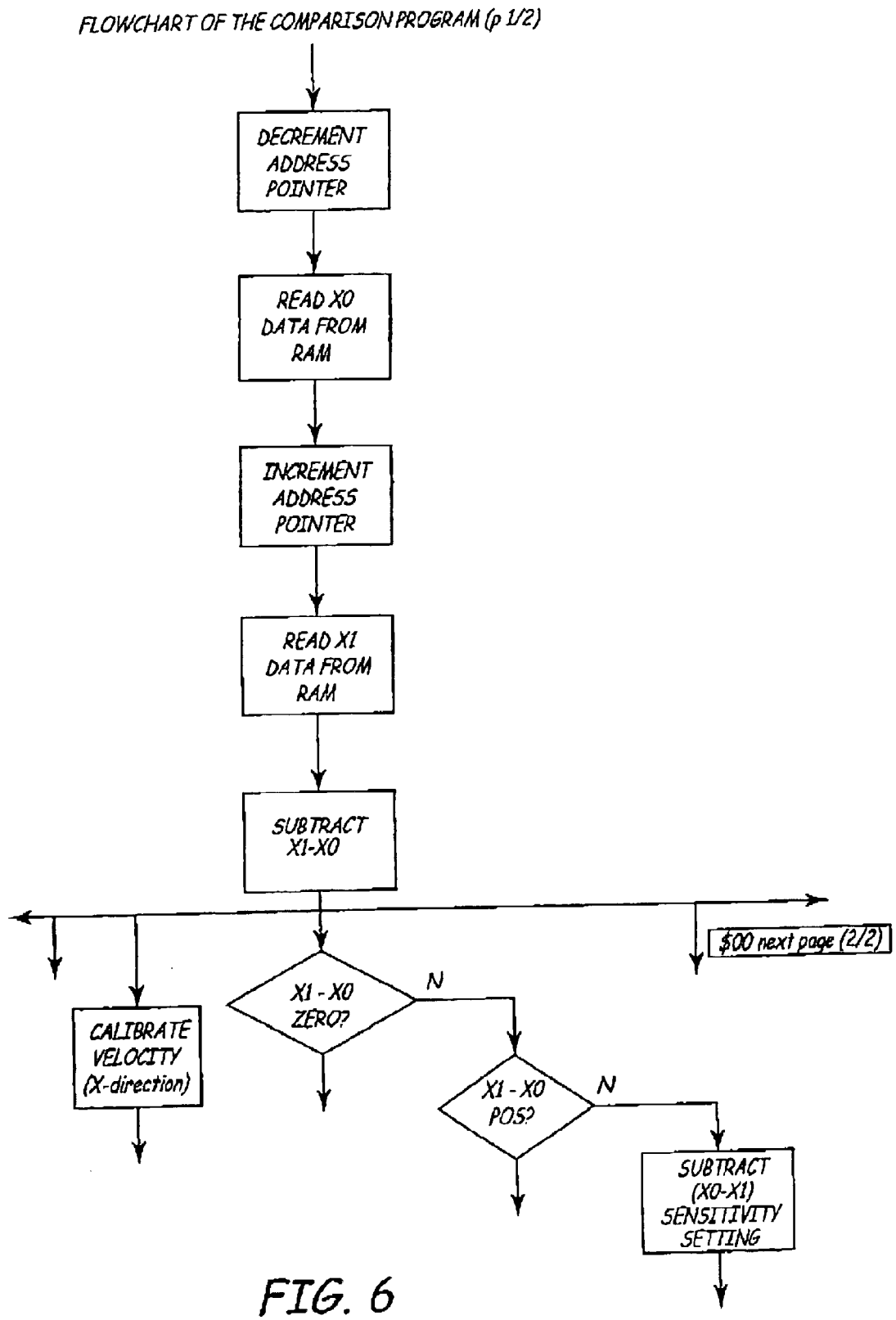
FIG. 6 shows a first portion flowchart of a comparison program.
Figure 7:
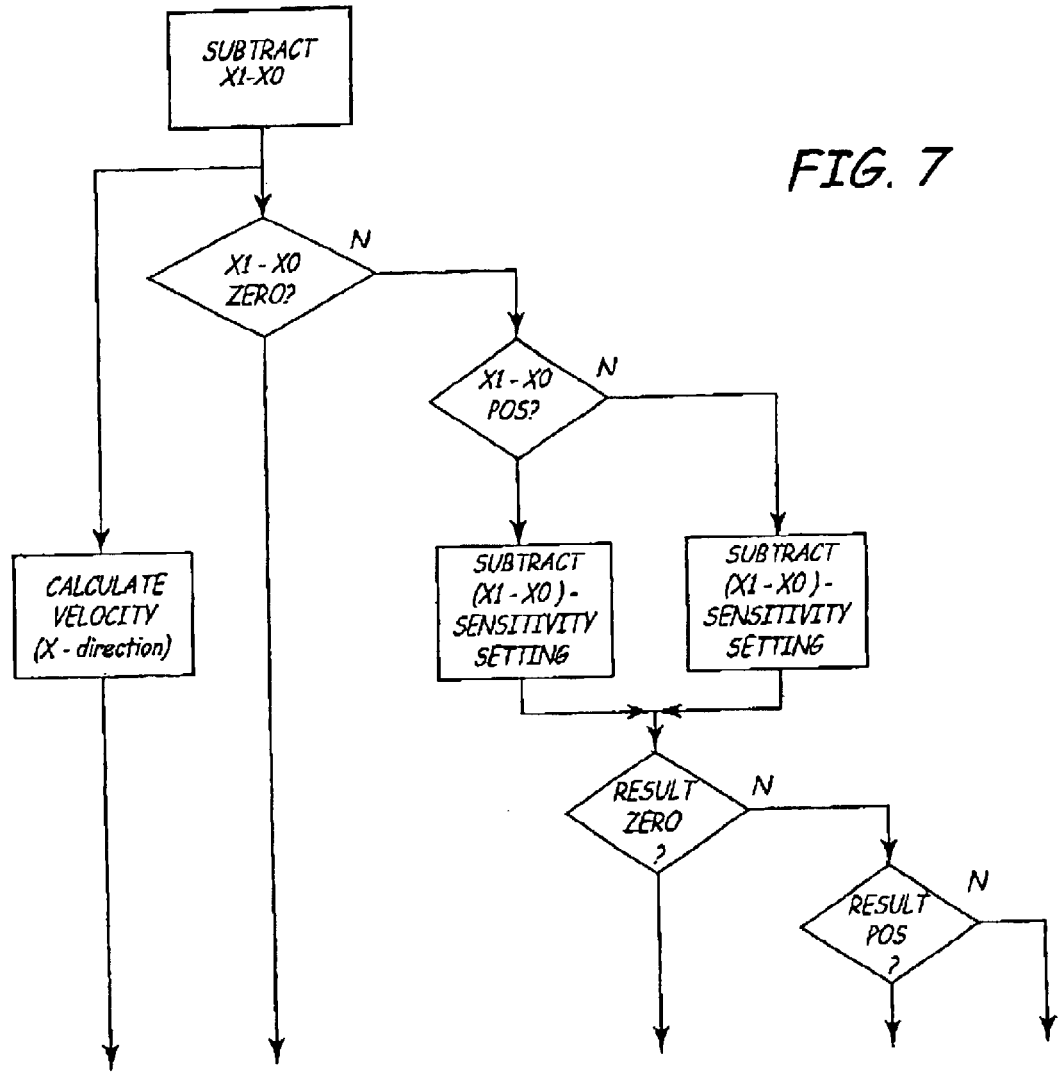
FIG. 7 shows a second portion flowchart of the comparison program.

FIGS. 6–7 show a flowchart of the comparison program 50. The comparison program 50 resides in memory 40 and compares ablation catheter 20 movement to predetermined control data and calculates the difference between the electrode position data frames for X, Y and Z coordinates. The comparison program 50 decrements the address pointer to locate the position where the first frame is stored in RAM. The first frame X-axis data (X0) is read from RAM. The address pointer is incremented and the second frame X-axis data (X1) is read from RAM. The first frame X-axis data (X0) is subtracted from the second frame X-axis data (X1) to calculate X axis position change. The result of the subtraction can be zero, positive or negative. Out of the X-axis position change, velocity can be calculated along the X-axis. If the result of the subtraction is positive, the sensitivity setting, i.e. the allowed change of position selected by the operator, is subtracted [(X1−X0)−sensitivity setting]. If the result of the subtraction is negative, the sensitivity setting is subtracted from (X0−X1) to ensure that always a positive result from the subtraction of X0 and X1 is used for the subtraction with the sensitivity setting. The result of the subtraction with the sensitivity setting can be zero, i.e. the change in position along the X-axis is exactly that of the allowed limit, negative, i.e. the change in position is smaller than the allowed limit, or positive, i.e. the change in position is higher than the allowed limit (dislocation). The same routine and calculations are to be performed for the Y-axis and the Z-axis. Predetermined control data, as referred to the sensitivity settings, can be between 1.0 and 10.0 cm/sec and is typically the allowed limit for catheter electrode displacement.

Figure 8:
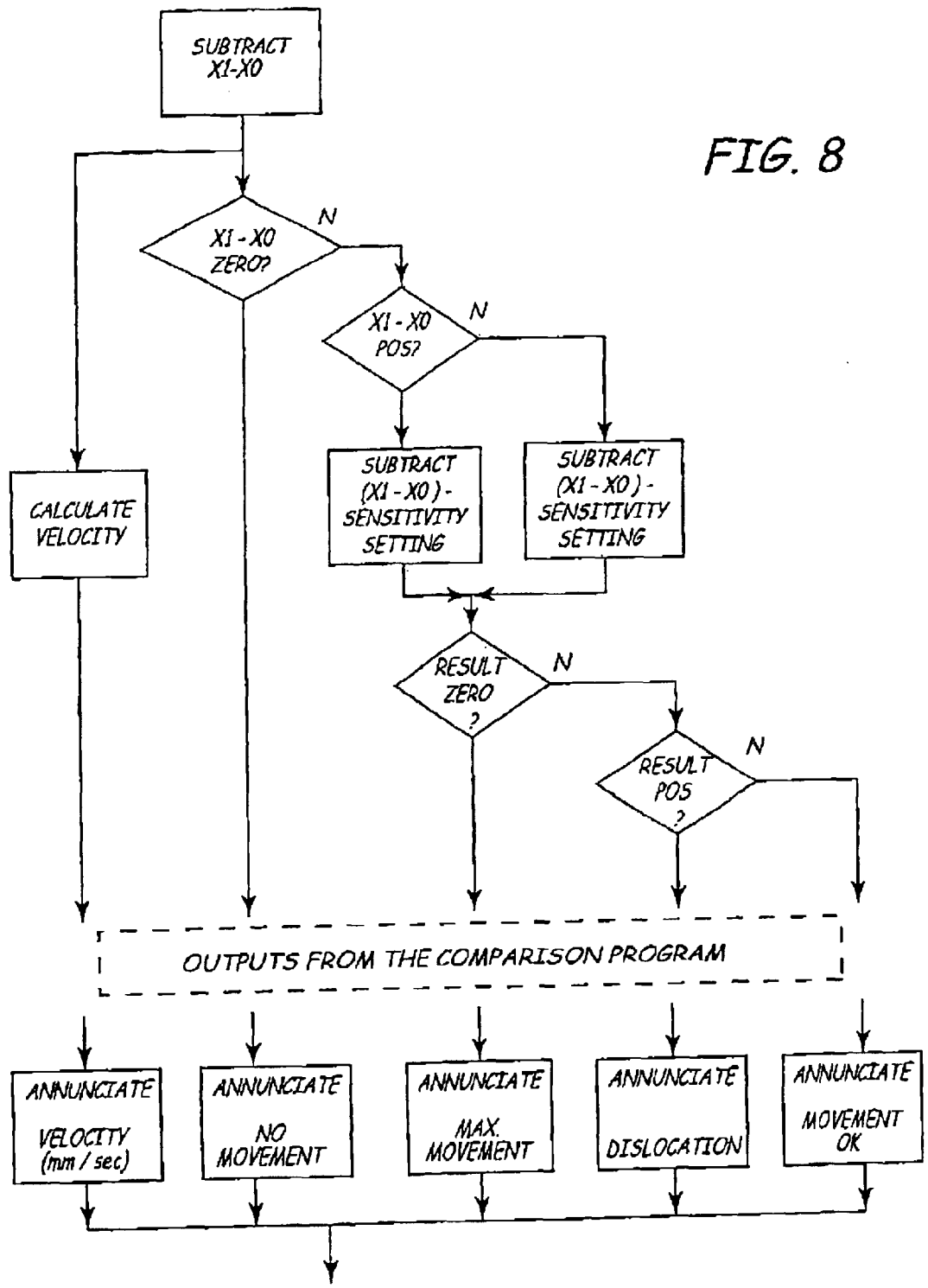
FIG. 8 shows a flowchart of an annunciating program.

FIG. 8 shows a flowchart of the annunciating program 52. The annunciating program 52 resides in memory 40 and is coupled to the outputs of the comparison program. The annunciating program 52 indicates the relation of ablation catheter 20 movement to the predetermined control data and displays the catheter electrode velocity in mm/sec in X, Y and Z direction. The annunciating program 52 can also indicate predetermined messages such as "no movement", "max. movement", "movement within predetermined boundaries", "movement exceeds predetermined boundaries", "catheter dislocation", and the like.

Figure 9:
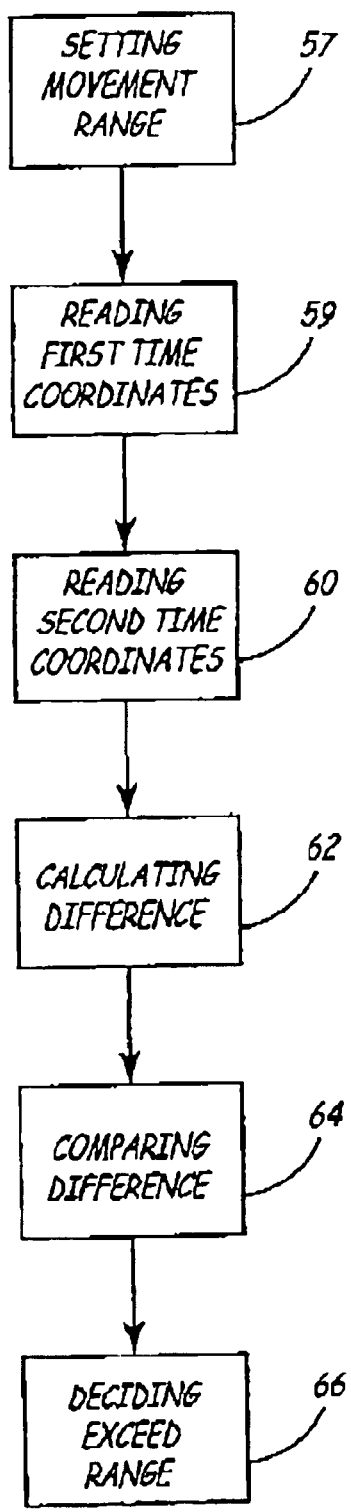
FIG. 9 shows a broad flowchart of a control program.
Figure 10:
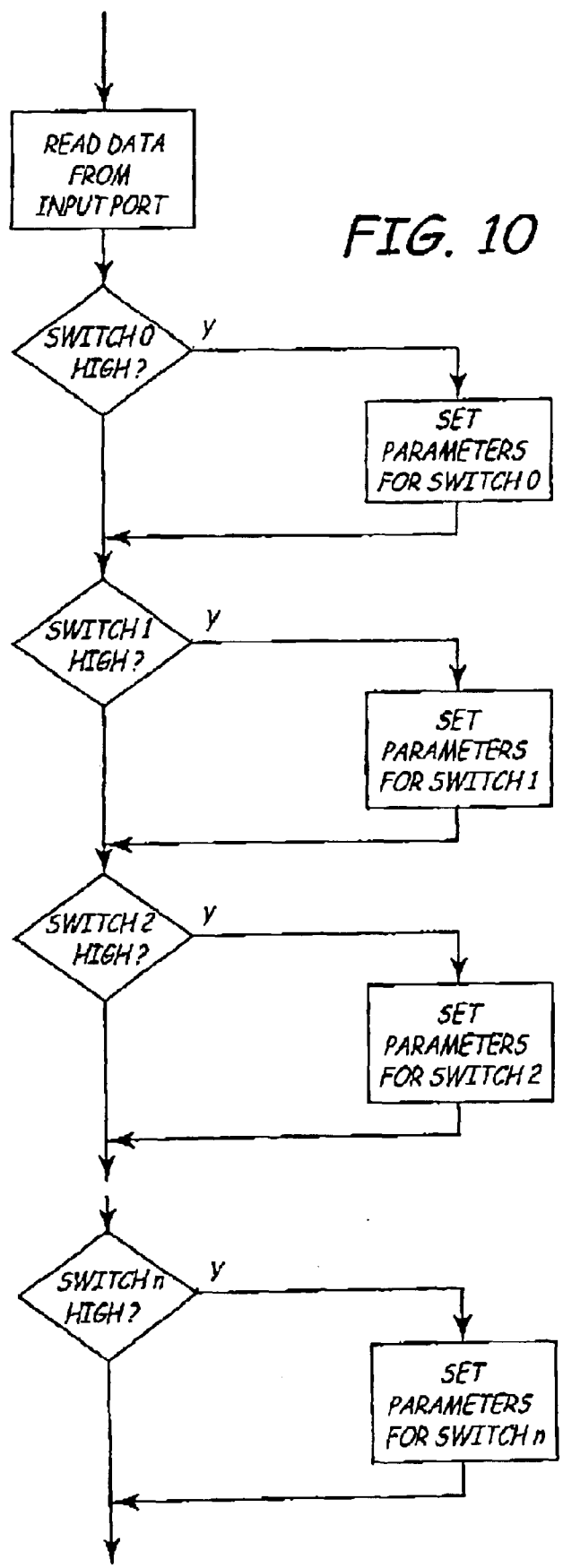
FIG. 10 shows a more detailed flowchart of the control program.

FIGS. 9–10 show a flowchart of the control program 54. The control program 54 resides in memory 40 and reads user settings and predetermined control data. A predetermined movement range is set 57 in some embodiments using switches 34 that correspond to control parameters. A first time, a first x axis coordinate, a first y axis coordinate, and a first z axis coordinate are read 59. At a second time, a second x axis coordinate, a second y axis coordinate, and a second z axis coordinate are read 60. A difference is calculated 62 between the first x axis coordinate and the second x axis coordinate, the first y axis coordinate and the second y axis coordinate, and the first z axis coordinate and the second z axis coordinate. The difference is compared 64 with the predetermined movement range. A decision 66 is made concerning whether an ablation catheter 20 has exceeded the predetermined movement range.

Figure 11:
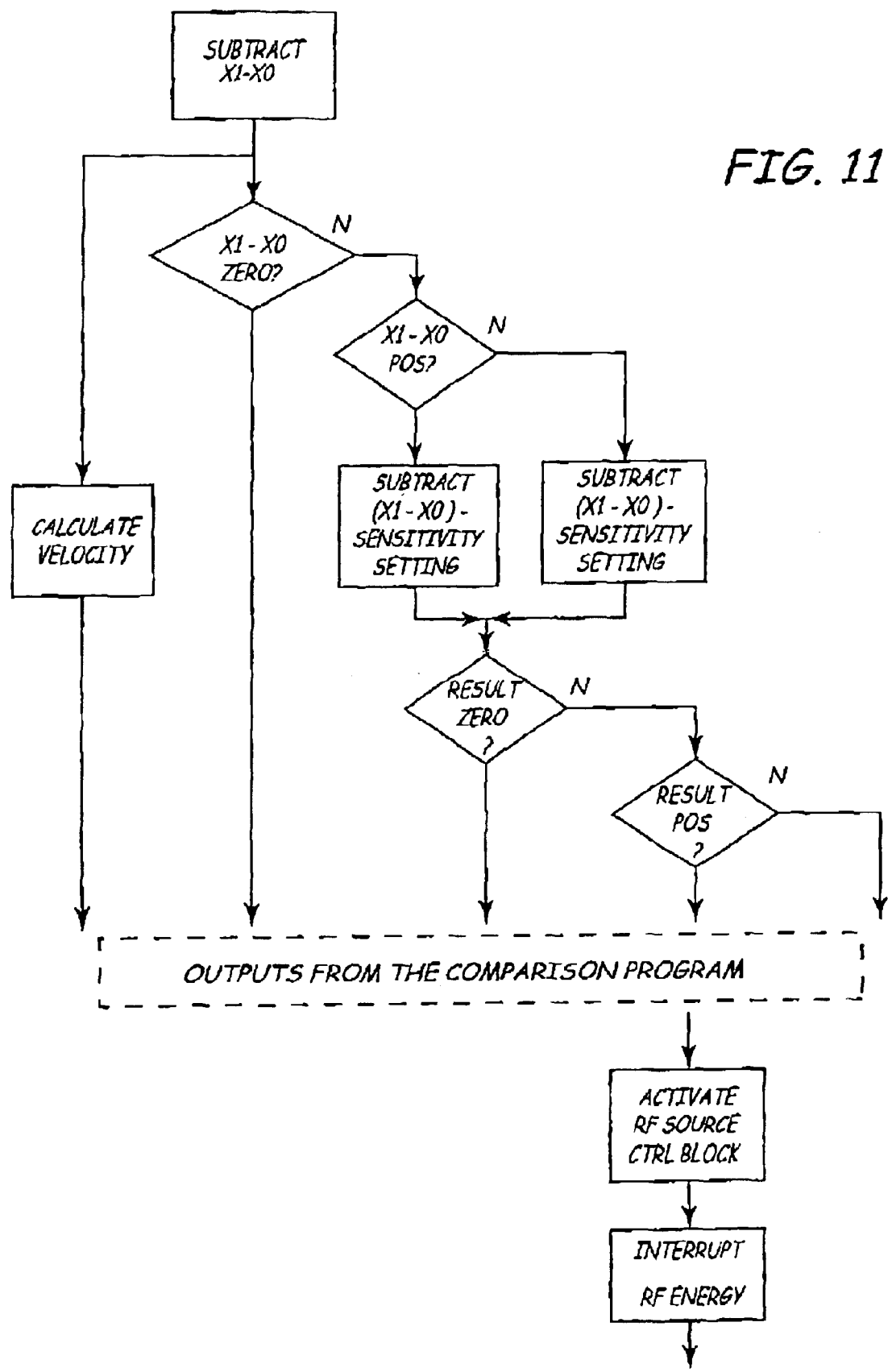
FIG. 11 shows a flowchart of a response program.

FIG. 11 shows a flowchart of the response program 56. The response program 56 resides in memory 40 and is coupled to one of the outputs of the comparison program. The response program 56 activates RF source control block and interrupts RF energy to the ablation catheter 20 when ablation catheter 20 movement exceeds the predetermined movement range. The response program 56 can interrupt power to the ablation catheter 20 in less than 500.0 ms after determining that movement has exceeded the predetermined value. In some versions, the response program 56 can interrupt power in as little as 1.0 ms.

Figure 12:
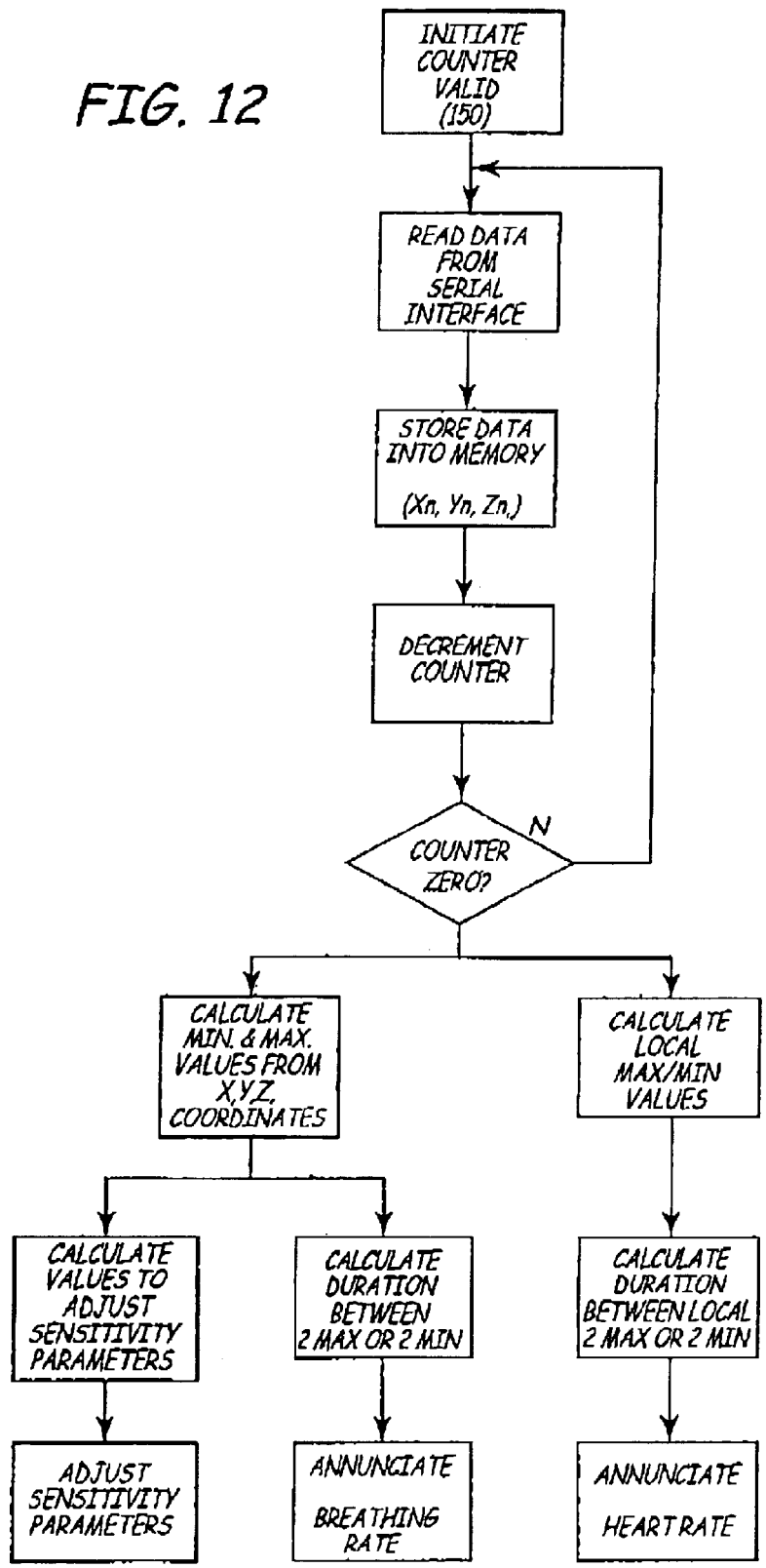
FIG. 12 shows a flowchart of a physiological movement program.
Figure 14:
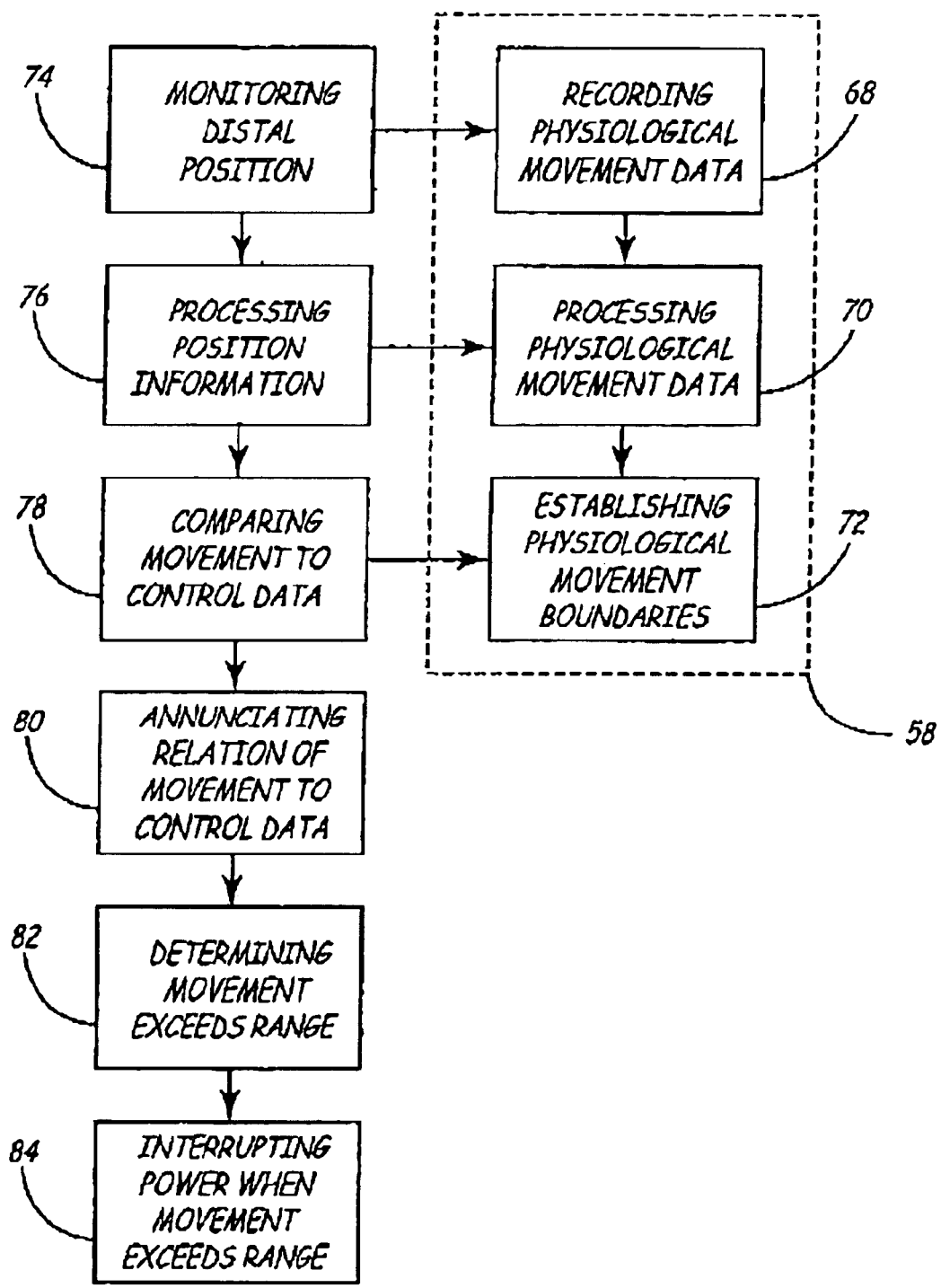
FIG. 14 shows a flowchart of a method for ablation catheter control.

FIG. 12 shows a flowchart of the physiological movement program 58, and FIG. 14 shows the physiological movement program 58 in relation to a method for ablation control. The physiological movement program 58 establishes a physiological movement baseline. The physiological movement baseline can be used to calculate respiratory rate and heart rate. The physiological movement program 58 comprises recording 68 physiological movement data and processing 70 physiological movement data. Physiological movement data is recorded over a period of time X coordinates, Y coordinates and Z coordinates while the ablation catheter position remains substantially unchanged. Physiological movement data is processed to determine a physiological movement baseline. Physiological movement boundaries are established 72 and can be used to adjust the predetermined movement control data. More specifically, the physiological movement program initiates the counter value, e.g. 150, meaning that 150 position data frames will be stored into memory. A first position data frame with X, Y, and Z position data will be read from the serial interface and stored into data memory. The counter is decremented by one and another data frame is read and stored. This will be repeated until the counter is zero (150 position data frames have been read and stored). Out of these position data frames, the minimal and maximal values for X, Y, Z position data are calculated. The maximal and minimal values can be used to calculate an adjusted sensitivity setting and to adjust the sensitivity parameters. The duration between 2 Maximal or Minimal values can be used to calculate and annunciate breathing rate. The duration between 2 local Maximal and Minimal values can be used to calculate and annunciate heart rate.

Figure 13:
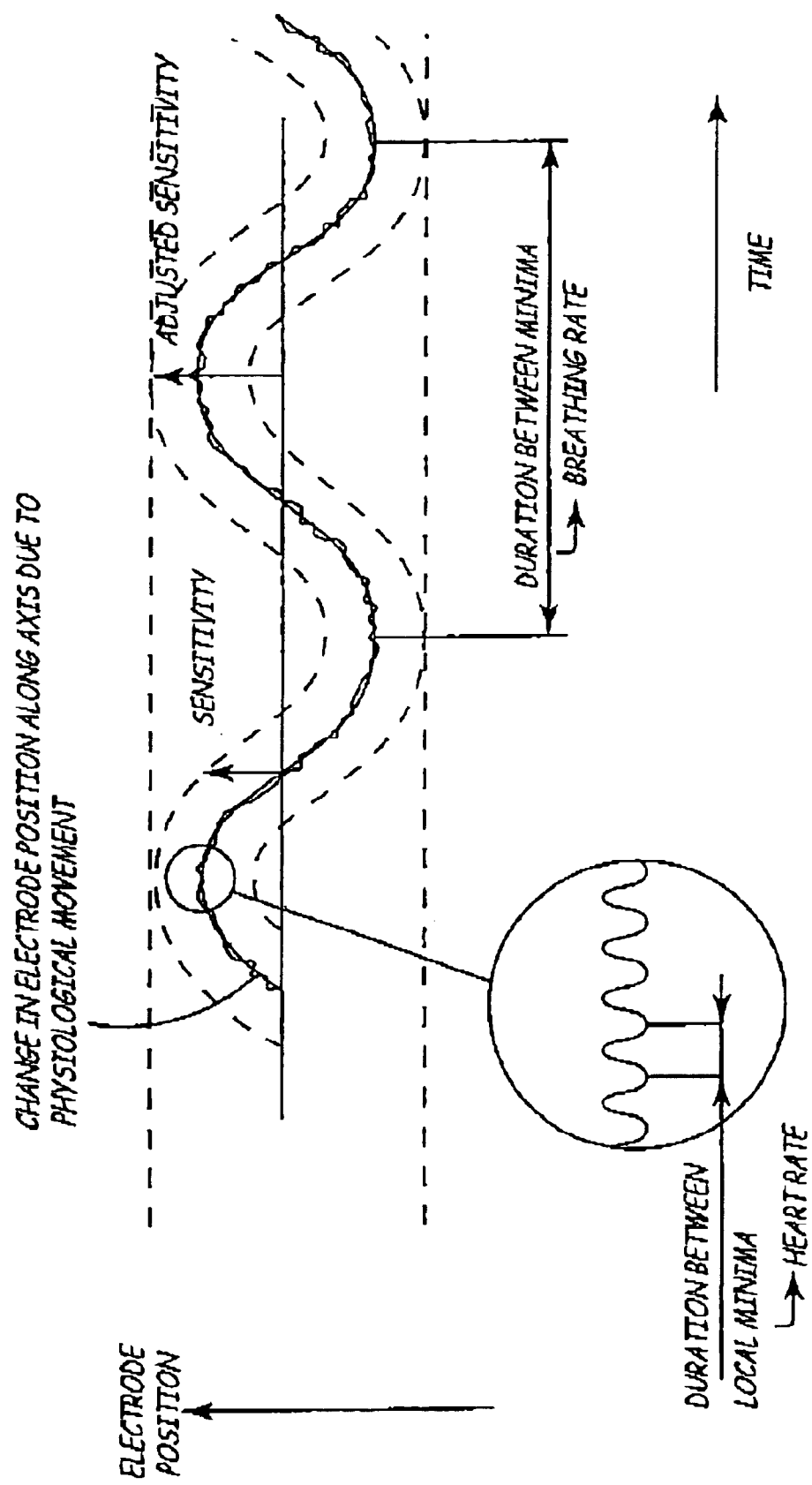
FIG. 13 shows a graph of electrode position changes due to physiological movement.

FIG. 13 shows a drawing of the change in electrode position along the axis due to physiological movement. The physiological movement is related to the beating of the heart and the breathing of the patient. The physiological movement program 58 establishes a physiological movement baseline during an unchanged catheter position. Out of these position data frames, the minimal and maximal values for X, Y, Z position data are calculated. These calculated values can be used to adjust the sensitivity parameters. The adjusted sensitivity can be calculated as:

$$\text{Adjusted Sensitive Setting} = \text{SensitivitySetting} + \left[ \frac{(MaximalValue - MinimalValue)}{2} \right] \quad \text{Equation 1}$$

Other embodiments of the adjusted sensitive setting can be performed with other mathematical adjustments. The duration between 2 Maximal or Minimal values can be used to calculate breathing and annunciate breathing rate. The breathing rate per minute can be calculated as follows:

$$\text{Breathing Rate} = \frac{60}{\text{Duration Between 2 Maxima/Minima}} \quad \text{Equation 2}$$

Local Maximal and Minimal values, between 2 Maximal or 2 Minimal values (in seconds), can be determined and the duration between local maximal or 2 minimal values can be used to calculate and annunciate heart rate. The heart rate per minute can be calculated as follows:

$$\text{Heart Rate} = \frac{60,000}{\text{Duration Between Local Maxima/Minima}} \quad \text{Equation 3}$$

FIG. 14 shows a flowchart of a method for ablation catheter control 26. The method begins with positioning an ablation catheter 20. The distal position of the ablation catheter is monitored 74 with an electronic position detection system that generates position information. Position information is processed 76 to calculate ablation catheter movement. Ablation catheter movement is compared 78 to predetermined control data. The relation of ablation catheter movement to the predetermined control data is annunciated 80. Some embodiments of the method can also include the following elements. Once ablation catheter movement is compared to predetermined control data, a determination 82 can also be made of whether ablation catheter movement exceeds a predetermined movement range. Power to the ablation catheter can be interrupted 84 when movement exceeds the predetermined movement range. Physiological movement data can be recorded over a period of time x coordinates, y coordinates and z coordinates while the ablation catheter position remains substantially unchanged. Physiological movement data can be processed to determine a physiological movement baseline. Physiological movement boundaries can be established 72 according to the physiological movement baseline.

Figure 15:
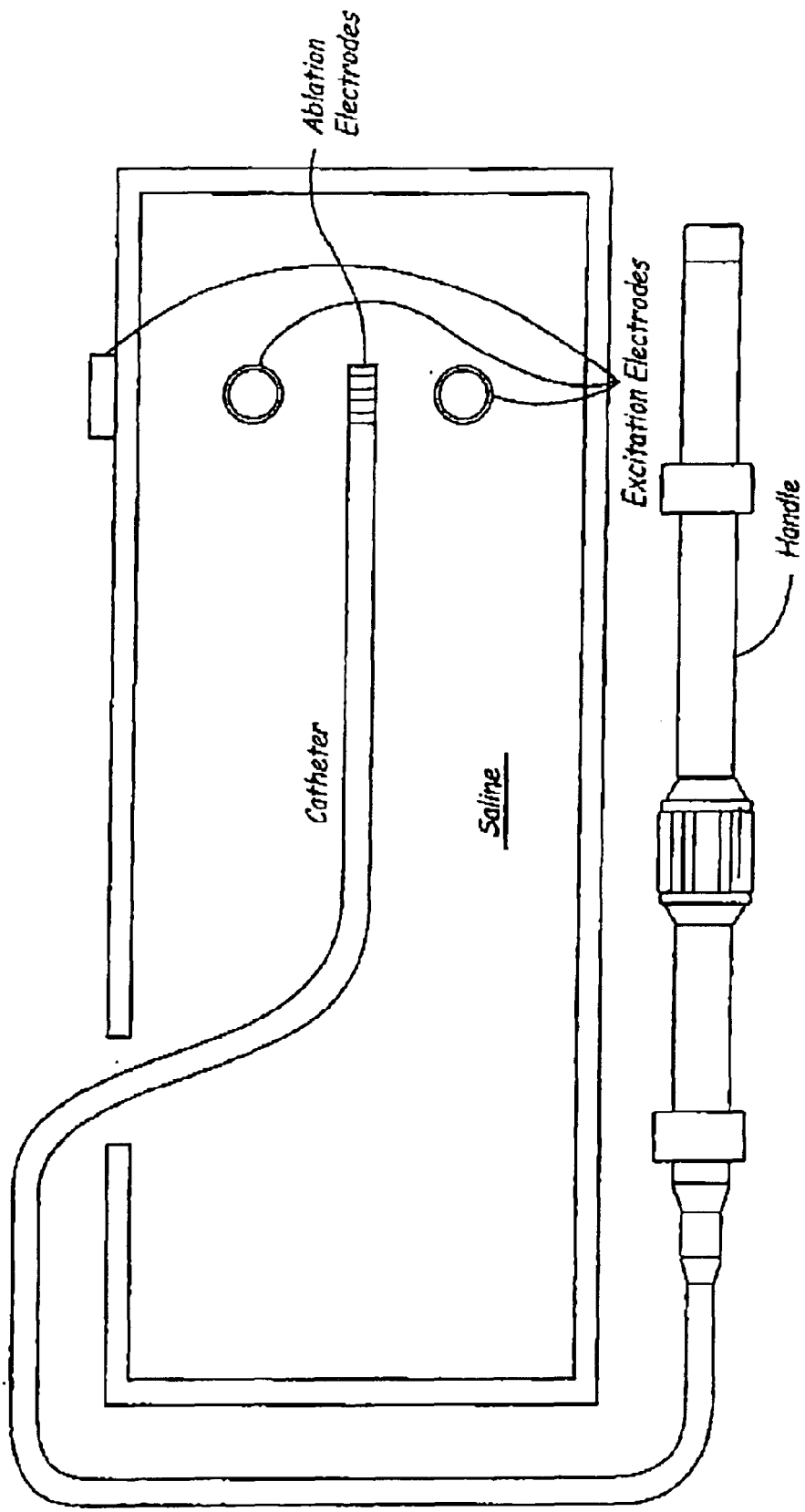
FIG. 15 shows the experimental tank setup.
Figure 16:
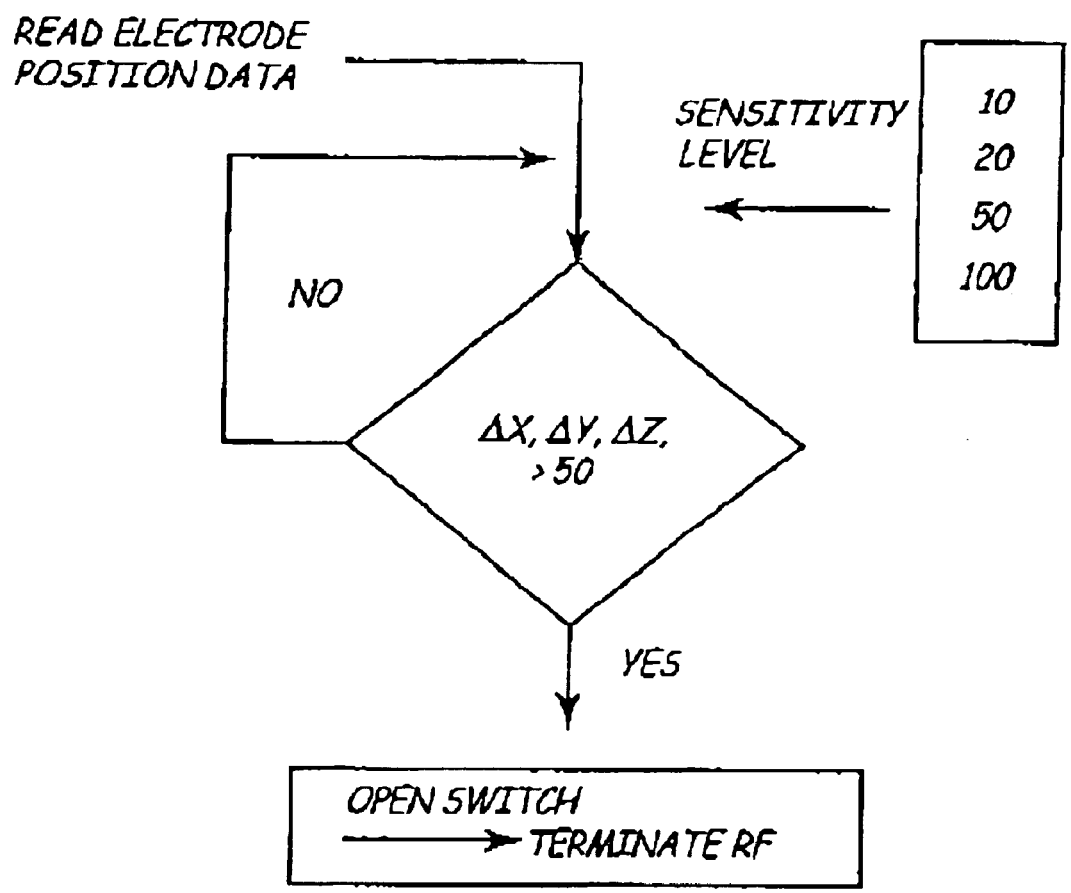
FIG. 16 shows an operational flowchart of the medical ablation catheter control as used in the experimental task setup in FIG. 15.

FIG. 15 shows the experimental tank setup. The tank was filled with saline solution simulating the patient. Distance markers on the catheter 20 shaft were used for different speeds of electrode movement by manually dragging for a certain time along the appropriate distance. LocaLisa electrodes providing the excitation current. FIG. 16 shows an operational flowchart of the medical ablation catheter control as used in the preliminary experiments with a first prototype.

An embodiment of the invention was developed and tested that initiates termination of RF delivery automatically upon catheter dislocation. The embodiment consisted of a microprocessor connected between the indifferent cable of the RF generator and the indifferent electrode (FIG. 2). The software program was developed using Microchip-MPLAB. This software inside the microprocessor continuously evaluates the X, Y and Z position information collected from the LocaLisa system that is transmitted at 9600 bits per second and updated ten times per second thus a change in electrode position can be detected within 200 ms. Four different sensitivity levels were programmed, i.e. 10, 20, 50 and 100. A sensitivity level of 10 allows a change in electrode position in either X, Y and Z direction of +/−10 mV without interaction by the embodiment of the invention. A red light indicates a sudden change within 200 ms of greater than the selected sensitivity level and an electronic switch is activated by the software to interrupt the connection between the indifferent electrode and the RF generator resulting in a high impedance shutdown and termination of RF energy delivery. Assuming a field strength of 50 mV/cm, the sensitivity values correspond to an electrode movement of 0.2 cm, 0.4 cm, 1 cm and 2 cm, respectively. This translates into speeds of electrode movement of 1 cm/sec, 2 cm/sec, 5 cm/sec and 10 cm/sec, respectively, considering the duration of 200 ms in which this movement must occur in order to initiate termination of RF energy.The RF safety device was connected according to FIG. 2 and tested in an in vitro tank simulating the patient. The LocaLisa electrodes, applying the 1.0 mA current, were connected at the tank having a connection to the inner of the tank that was filled with isotonic saline solution. The ablation catheter (RF Marinr, Medtronic EPSystems) was positioned inside the tank and connected to the RF generator (Atakr II, Medtronic EPSystems). During a constant RF power delivery of 25 W the catheter was manually withdrawn with a dragging speed of either 0.5, 1, 2, 5, 10, 15 or 20 cm/sec. and the reaction of the RF safety device was documented. Distance markers on the catheter shaft were used for different speeds of electrode movement by manually dragging for 1 second along the appropriate distance.

Every setting was repeated three times. For the sensitivity levels 10, 20, 50 and 100, an immediate termination of RF delivery was observed for an electrode dragging speed of greater or equal than 1 cm/sec, 2 cm/sec, 5 cm/sec and 10 cm/sec, respectively. The termination of RF delivery was achieved by an automatic shutdown of the generator due to an impedance of greater than 250Ω.

Embodiments of the medical ablation control catheter are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A medical ablation catheter control structure, comprising:
   a microcontroller containing memory;
   an input coupled to the microcontroller, the input configured for receiving position information of an ablation catheter from an electronic position detection system;
   an output coupled to the microcontroller; the output configured for communicating ablation catheter movement;
   a movement program residing in memory, the movement program processing position information from the input to calculate ablation catheter movement;
   a comparison program residing in memory, the comparison program compares ablation catheter movement to a predetermined control data; and,
   an annunciating program means residing in memory and coupled to the output for indicating a spatial relationship between the ablation catheter and the predetermined control data and in the event that the spatial relation exceeds a threshold value for interrupting a source of ablative energy to the ablation catheter.

2. The medical ablation catheter control structure as in claim 1 further comprising,
   a control program residing in memory, the control program determining when ablation catheter movement exceeds a predetermined movement range; and,
   a response program residing in memory and coupled to the output, the response program interrupting power to the ablation catheter when ablation catheter movement exceeds the predetermined movement range.

3. The medical ablation catheter control structure as in, claim 2 wherein interrupting power to the ablation catheter is accomplished in less than 500 ms after determining that movement has exceeded the predetermined value.

4. The cardiac ablation catheter control structure as in claim 2 wherein the control program comprises,
   setting the predetermined movement range;
   reading at a first time a first x axis coordinate, a first y axis coordinate, and a first z axis coordinate,
   reading at a second time a second x axis coordinate, a second y axis coordinate, and a second z axis coordinate;
   calculating a difference between the first x axis coordinate and the second x axis coordinate, the first y axis coordinate and the second y axis coordinate, and the first z axis coordinate and the second z axis coordinate;
   comparing the difference with the predetermined movement range; and,
   deciding whether an ablation catheter has exceeded the predetermined movement range.

5. The cardiac ablation catheter control structure as in claim 4 wherein determining whether movement has exceeded the predetermined movement range is accomplished in less than 500 ms after movement has occurred.

6. The medical ablation catheter control structure as in claim 1 wherein ablation catheter movement includes ablation catheter velocity.

7. The medical ablation catheter control structure as in claim 2 further comprising a physiological movement program to establishing a physiological movement baseline.

8. The medical ablation catheter control structure as in claim 7 wherein the physiological movement program comprises,
   recording physiological movement data over a period of time x coordinates, y coordinates and z coordinates while the ablation catheter position remains substantially unchanged;
   processing physiological movement data to determine a physiological movement baseline; and,
   establishing physiological movement boundaries according to the physiological movement baseline.

9. The medical ablation catheter control structure as in claim 7 wherein the physiological movement baseline is used to calculate respiratory movement and heart movement.

10. A method for medical ablation catheter control, comprising:
    positioning an ablation catheter;
    monitoring distal position of the ablation catheter with an electronic position detection system that generates position information;
    processing position information to calculate ablation catheter movement;
    comparing ablation catheter movement relative to a predetermined control data set;
    annunciating relation of ablation catheter movement to the predetermined control data; and
    one of reducing and interrupting a source of energy the ablation catheter in the event that the catheter movement exceeds a threshold value.

11. The method as in claim 10 further comprising,
    recording physiological movement data over a period of time x coordinates, y coordinates and z coordinates while the ablation catheter position remains substantially unchanged;
    processing physiological movement data to determine a physiological movement baseline; and,
    establishing physiological movement boundaries according to the physiological movement baseline.

12. A method of controlling a medical electrophysiology mapping and ablation catheter, comprising:
    positioning a medical mapping/ablation catheter within a portion of a heart;
    monitoring a position of the catheter with an electronic position detection system that generates position information regarding a distal portion of the catheter;
    processing position information to calculate catheter movement;
    comparing catheter movement relative to a predetermined control data set;
    annunciating relation of ablation catheter movement to the predetermined control data; and
    one of reducing and interrupting a source of energy to the catheter in the event that the catheter movement exceeds a threshold value of said control data set.

13. A method according to claim 12, further comprising:
    producing a warning signal in the event that the position of the distal portion of the catheter no longer is disposed within the portion of the heart.

14. A method according to claim 13, wherein the warning signal comprises at least one of: an audible warning signal, a tactile warning signal, a visibly perceptible warning signal.

15. A method according to claim 12, further comprising:
producing a warning signal in the event that the position of the distal portion of the catheter fails to advance at a predetermined rate.

16. A method according to claim 15, wherein the warning signal comprises at least one of: an audible warning signal, a tactile warning signal, a visibly perceptible warning signal.

17. A method according to claim 12, further comprising:
displaying both a heart rate and a breathing rate of a patient from based at least in part upon the calculated catheter movement.

18. A method according to claim 17, further comprising terminating an ablation energy delivery sequence to the catheter in the event that the heart rate decreases.

19. A method according to claim 12, wherein the step of reducing and interrupting a source of energy to the catheter comprises at least one of; inserting a high impedance load intermediate at least two members of the group:

a high energy ablation generator, an indifferent electrode, a electrode localization system.

* * * * *